US006863660B2

(12) United States Patent
Marx

(10) Patent No.: US 6,863,660 B2
(45) Date of Patent: Mar. 8, 2005

(54) FIBRIN APPLICATOR PISTOL

(75) Inventor: Gerard Marx, Jerusalem (IL)

(73) Assignee: Hapio Biotech, Inc., Garden City, NY (US)

(*) Notice: Subject to any disclaimer, the term of this patent is extended or adjusted under 35 U.S.C. 154(b) by 222 days.

(21) Appl. No.: 10/107,678

(22) Filed: Mar. 27, 2002

(65) Prior Publication Data

US 2003/0187408 A1 Oct. 2, 2003

(51) Int. Cl.[7] .......................... A61M 37/00; A61M 31/00; A61M 11/00

(52) U.S. Cl. .......................... 604/147; 604/82; 604/275; 128/200.23

(58) Field of Search .............................. 604/82, 83, 85, 604/93.01, 131, 140, 141, 146, 147, 264, 275; 606/213, 214; 128/200.14, 200.21, 200.23; 222/145.1, 145.5

(56) References Cited

U.S. PATENT DOCUMENTS

| | | | |
|---|---|---|---|
| 2,533,004 | A | 12/1950 | Ferry et al. |
| 4,040,420 | A | 8/1977 | Speer |
| 4,359,049 | A | 11/1982 | Redl et al. |
| 4,631,055 | A | 12/1986 | Redl et al. |
| 4,735,616 | A | 4/1988 | Eibl et al. |
| 4,874,368 | A | 10/1989 | Miller et al. |
| 4,902,281 | A | 2/1990 | Avoy |
| 4,978,336 | A | 12/1990 | Capozzi et al. |
| 4,979,942 | A | 12/1990 | Wolf et al. |
| 5,185,001 | A | 2/1993 | Galanakis |
| 5,290,259 | A | 3/1994 | Fischer |
| 5,368,563 | A | 11/1994 | Lonneman et al. |
| 5,376,079 | A | 12/1994 | Holm |
| 5,411,885 | A | 5/1995 | Marx |
| 5,474,540 | A | 12/1995 | Miller et al. |
| 5,535,950 | A | 7/1996 | Barriac et al. |
| 5,582,596 | A | 12/1996 | Fukunaga et al. |
| 5,711,457 | A | 1/1998 | Wanbaugh et al. |
| 5,752,626 | A | 5/1998 | Bachand |

(List continued on next page.)

FOREIGN PATENT DOCUMENTS

| | | |
|---|---|---|
| EP | 0 839 498 A1 | 5/1998 |
| EP | 0 858 775 A1 | 8/1998 |
| WO | WO 96/17638 | 6/1996 |
| WO | WO 98/02098 | 1/1998 |
| WO | WO 98/40167 | 9/1998 |
| WO | WO 99/022Q7 | 1/1999 |
| WO | WO 99/17833 | 4/1999 |
| WO | WO 99/56815 | 11/1999 |
| WO | WO 00/01035 | 1/2000 |
| WO | WO 00/01305 | 1/2000 |

OTHER PUBLICATIONS

D. J. Bryne—Effect of Fibrin Glues on the Mechanical Properties of Healing Wounds—Br. J. Surg. 1991, vol. 78, Jul., 841–843.

(List continued on next page.)

*Primary Examiner*—Nicholas D. Lucchesi
*Assistant Examiner*—Mark K Han
(74) *Attorney, Agent, or Firm*—Amster, Rothstein & Ebenstein LLP

(57) ABSTRACT

An applicator for dispensing a first and second component of a biological adhesive, such as fibrin glue. At least one of said components may contain a suspension of fibrin microbeads (FMB) or a suspension of cells. The present invention uses a single supply of pressurized gas to force the components from the applicator using positive fluid pressure and to atomize them into a convergent spray. Another embodiment of the present invention also provides for the endoscopic application of the biological adhesive directly to tissue defects. The application of positive pressure allows precise metering of the components and application of the adhesive, prevents internal coagulation of the fibrin or clogging by suspended particles and reduces waste and contamination of the components.

45 Claims, 10 Drawing Sheets

U.S. PATENT DOCUMENTS

| | | | |
|---|---|---|---|
| 5,759,169 | A | 6/1998 | Marx |
| 5,759,171 | A | 6/1998 | Coelho et al. |
| 5,810,885 | A | 9/1998 | Zinger |
| 5,976,102 | A | 11/1999 | Epstein |
| 5,989,215 | A | 11/1999 | Delmotte et al. |
| 6,007,515 | A | 12/1999 | Epstein et al. |
| 6,059,749 | A | 5/2000 | Marx |
| 6,063,055 | A | 5/2000 | Epstein et al. |
| 6,113,571 | A | 9/2000 | Zinger et al. |
| 6,132,396 | A | 10/2000 | Antanavich et al. |
| 6,150,505 | A | 11/2000 | Marx et al. |
| 6,228,051 | B1 | 5/2001 | Trumbull |
| 6,234,994 | B1 | 5/2001 | Zinger |

OTHER PUBLICATIONS

David H. Sierra—Failure Characteristics of Multiple–Component Fibrin–based Adhesives—Sep. 2001; DOI 10, 1002/jbm.1210.

Richard L. Burelson, M.D., FACS,—Fibrin Adherence to Biologic Tissues—Journal of Surgical Research (1978).

MARX—Kinetic and Mechanical Parameters of Pure and Cryoprecipitate Fibrin—Blood Coagulation and Fibrinolysis, vol. 4, 1993.

Robert P. Sanders, B.S.—Effect of Fibrinogen and Thrombin Concentrations on Mastecotomy Seroma Prevention—Journal of Surgical Research (1996).

B. M. Alving—Fibrin Sealant: Summary of a Conference on Characteristics and Clinical Uses—Trunsfustion 1995; 35:783–790.

Robert P. Sanders, B.S.,—Effect of Fibrinogen and Thrombin Concentrations on Mastectomy Seroma Prevention—Journal of Surgical Research 61, 76–70 (1996).

B.M. Alving—Fibrin Sealant: Summary of a Conference on Characteristics and Clinical Uses—Transfusion 1995;35.:83–790.

M. Radosevich—Fibrin Sealant: Scientific Rationale, Production Methods, Properties, adn Current Clinical Uses—Vox Sang 1997;72:133–143.

Raphael Gorodetsky—Haptotactic and Growth Stimulatory Effects of Fibrin (ogen) and Thrombin on Cultured Fibroblasts—0022–2143/98.

Raphael Gorodetsky—Fibrin Microbeads (FMB) as Biodegradable Carriers for Culturing Cells and for Accelerating Wound Healing—0022–202X/99.

Gerard Marx—Characterizing fibrin Glue Performance as Modulated by Heparin, Aprotinin, and Factor XIII—0022–2143/2002.

Raphael Gorodetsky—Fibrin Nanobeads (FNB) for Cell Targeting—Jan. 15, 2001.

A. Blinc—Atomic Force Microscopy of Fibrin Networks and Plasma Clots During Fibrinolysis—Fibrinolysis & Proteolysis (2000) 14(5) 288–299.

Carsten Perka, M.D.—Matrix–Mixed Culture: New Methodology for Chondrocyte Culture and Preparation of Cartilage Transplants—CCC—0021–9304/00/030305–07.

Carsten Perka, M.D., —The Use of Fibrin Beads for Tissue Engineering and Subsequential Transplantation—Tissue Engineering—vol. 7, No. 3, 2001.

Richard I. Senderoff,—Fibrin Based Drug Delivery Systems—Journal of Parenteral Science & Technology—1990.

Hsio–O Ho—Fibrin–Based Drug Delivery Systems. II. The Preparation and Characterization of Microbeads—1994.

FIBRIN APPLICATOR PISTOL

BACKGROUND OF THE INVENTION

I. Field of the Invention

The invention relates generally to a device and method for dispensing two discrete, chemically reactive components, such as fibrinogen and thrombin as either a convergent spray or in droplet form. More specifically, the instant invention is directed to a spraying apparatus and method for dispensing fibrin sealant containing particles in either spray or droplet form, to tissues, organs, wound sites, or prosthetic devices.

II. Description of Related Art

Fibrinogen mixed with thrombin forms fibrin, a unique biomaterial. In circulating blood, fibrin is critical for establishing normal hemostasis. The clinical utility of virally inactivated fibrin glue from pooled blood plasma is based upon its ability to effectively induce hemostasis and tissue bonding, in addition to being biodegradable and generally non-immunogenic.

Fibrin glue is formed by mixing two components, human fibrinogen (or a source of fibrinogen, such as freeze-dried plasma protein concentrate of fibrinogen/factor XIII) and an activating enzyme such as thrombin. Prior to use, the lyophilized protein concentrates are conventionally solubilized by adding water. Alternately, these components may be stored frozen and thawed prior to use. Thrombin-induced activation of fibrinogen results in the formation of fibrin. Factor XIII and calcium participate in the cross-linking and stabilization of fibrin to become a tight mesh of polymeric fibrin glue. Applied to tissue, the fibrin clot adheres to the site of application. The rate of coagulation and mechanical properties of the clot are dependent on the concentration of fibrinogen as well as thrombin. Traditional fibrin glue preparations are described in International Application No. WO93/05067 to Baxter International, Inc.; WO92/13495 to Fibratek, Inc.; and U.S. Pat. No. 5,607,694, (Marx, G., Biologic Bioadhesive Compositions Containing Fibrin Glue and Liposomes, Methods of Preparation and Use, Issued Jul. 29, 1997 which is hereby incorporated by reference).

Fibrin can also be transformed into other potent tools for cell culturing and tissue engineering. For example, fibrin has been described as a permeable, visco-elastic matrix useful for organ cultures (Marx G, Methods for Tissue Embedding and Tissue Culturing, U.S. Pat. No. 5,411,885 issued May 2, 1995 which is hereby incorporated by reference). Based on fibrin's positive interactions with numerous cell types, fibrin microbeads (FMB) have been developed as a cell-culture matrix useful for culturing many types of mesenchymal cells to high density (Gorodetsky, R., et al. J. Lab. Clin. Med. 131: 269–280 (1998) and Marx G, et al., Fibrin Microbeads Prepared from Fibrinogen, Thrombin and Factor XIII, U.S. Pat. No. 6,150,505, issued Nov. 21, 2000, which is hereby incorporated by reference). When cells bound to FMB suspended in fibrinogen are applied to tissue, the result is like a "liquid tissue" which may be used for regenerating skin, bone, and other tissue in situ.

However, because fibrinogen and thrombin are mutually reactive, have different viscosities, react efficiently with each other according to precise ratios, and are relatively precious commodities, complicated fibrin applicators have been developed that attempt, to varying degrees, and with limited success to address the need for an applicator that accommodates these characteristics.

Furthermore, the delivery of FMB or particles suspended within fibrinogen has proven particularly difficult. Given the several potential uses of FMB including as drug delivery systems, as vehicles for growing and transplanting cultured cells, and to promote wound healing, the incorporation of FMB delivery with the convergent application of the two components of fibrin glue requires an applicator that can deliver particles in suspension with the same accuracy and reliability as fibrinogen or thrombin alone. Such fibrin applicators are still lacking.

A few types of dual-channel applicators have been developed to deliver fibrin glue. Most designs have been based on a dual-syringe system wherein needles are used to extract the fibrinogen and thrombin solutions from vials. The vials and needles are discarded, and the loaded syringes are assembled into a unit docked onto a dual-cannula head. The twinned syringe plungers are then actuated with the thumb, and the twin streams of fibrinogen and thrombin are expelled as liquids which mix, either within the head or external to it. U.S. Pat. No. 4,354,049 to Redl et al., and U.S. Pat. No. 5,582,596 to Fukunaga et al. are examples of such applicators. Fukunaga et al. also teaches using an additional source of air to atomize the dual-liquid channels into a spray. Some variants of this utilize a dual-point head to form an atomized spray from thumb or trigger actuated syringes. U.S. Pat. No. 5,759,171 to Coelho et al. is an example of such an approach. Other applicators are operated by mechanically actuated atomizers such as those used in conventional spray pumps. U.S. Pat. No. 4,902,281 to Avoy uses such an approach wherein two pump-style atomizers are loaded with fibrinogen and thrombin and convergently aimed.

These approaches tend to suffer from clogging or the inability to deliver suspended particles. Also, the applicators of the prior art suffer from inconvenient loading, leakage, and inadequate mechanical control of delivery volume.

Still other designs utilize a positive gas and vacuum pressure to actuate or augment the delivery mechanism such as U.S. Pat. Nos. 6,007,515 and 6,063,055 to Epstein et al. Some designs rely upon a source of compressed gas to draw the fibrinogen and thrombin from separate reservoirs using the Bernoulli principle such as U.S. Pat. No. 6,059,749 to Marx. These designs also suffer from inconvenience of loading reservoirs and are highly complex from the standpoint of having many parts or circuitous fluid pathways that may not be appropriate for delivering very viscous solutions, or solutions containing suspended particles such as FMB.

Therefore, what is needed is a mechanically simple applicator with unhindered liquid pathways for efficiently delivering precise ratios of fibrinogen and thrombin with suspended particles to form on surface or internal wounds, a fibrin matrix containing such particles.

SUMMARY OF THE INVENTION

The present invention provides an applicator for delivering a homogeneous coating of a biological substance such as fibrin glue formed of two components, for example, fibrinogen and thrombin solutions carrying a suspension of FMB or cells. The applicator of the present invention provides: (a) a first hermetically scaled reservoir containing the first component; (b) a second hermetically sealed reservoir containing the second component; (c) a means for applying positive fluid pressure to each of the first and second reservoirs; (d) a first outlet conduit to carry the first component to an atomizer; and (e) a second outlet conduit to carry the second component to an atomizer; wherein pressure applied to the first and second reservoirs generates a convergent flow of the first and second components, resulting in a homogeneous coating applied to a surface.

The present invention also provides a method for delivering a homogeneous spray coating of a biological substance such as fibrin glue formed of two components such as fibrinogen and thrombin onto a target surface, such as human tissue. The method of the present invention comprises: (a) pressurizing a first reservoir containing one of said two components thereby biasing the component to flow from a first outlet conduit; (b) pressurizing a second reservoir containing the other of said two components thereby biasing the component to flow from a second outlet conduit; (c) atomizing the flows of the first and second component and (d) orienting the first and second outlet conduit so that the atomized flows of the components intermix to form the biological substance during deposition thereof.

The present invention further provides an applicator for delivering a biological substance such as fibrin glue formed of droplets of two components such as fibrinogen and thrombin solutions carrying a suspension of FMB or cells which mix immediately after exiting the applicator. The applicator of the present invention provides: (a) a first hermetically sealed reservoir containing the first component; (b) a second hermetically sealed reservoir containing the second component; (c) a means for applying positive fluid pressure to each of the first and second reservoirs; (d) a first outlet conduit to carry the first component to a first channel of a dual-cannula head; (e) a second outlet conduit to carry the second component to a second channel of a dual-cannula head; wherein pressure applied to the first and second reservoirs generates a convergent flow of the first and second components, resulting in a spray application of the biological substance.

The present invention still further provides a method for delivering a biological substance such as fibrin glue formed of droplets of two components such as fibrinogen and thrombin solutions carrying a suspension of FMB or cells which mix immediately after exiting the applicator. The method of the present invention comprises: (a) pressurizing a first reservoir containing one of said two components thereby biasing the component to flow from a first out let conduit; (b) pressurizing a second reservoir containing the other of said two components thereby biasing the component to flow from a second outlet conduit; (c) directing said first and second component respectively into a first and second channel of a dual cannula head oriented to produce a convergent flow of the first and second components, resulting in a topical droplet application of the biological substance.

Accordingly, it is an object of the present invention to provide an applicator that can reliably deliver two components of a biological adhesive at precise ratios whether or not the components carry a suspension of particles.

It is a further object of the present invention to provide a method for applying fibrin glue whereby FMB or cells become incorporated into a fibrin matrix as the fibrinogen and thrombin are combined as a spray to coat a target.

It is a further object of the present invention to provide a method for applying a fibrin matrix whereby FMB or cells become incorporated into a fibrin matrix formed as the fibrinogen and thrombin are combined as a mixed fluid applied topically (endoscopically) to a targeted wound area.

DETAILED DESCRIPTION OF THE PREFERRED EMBODIMENTS

Figure 1:
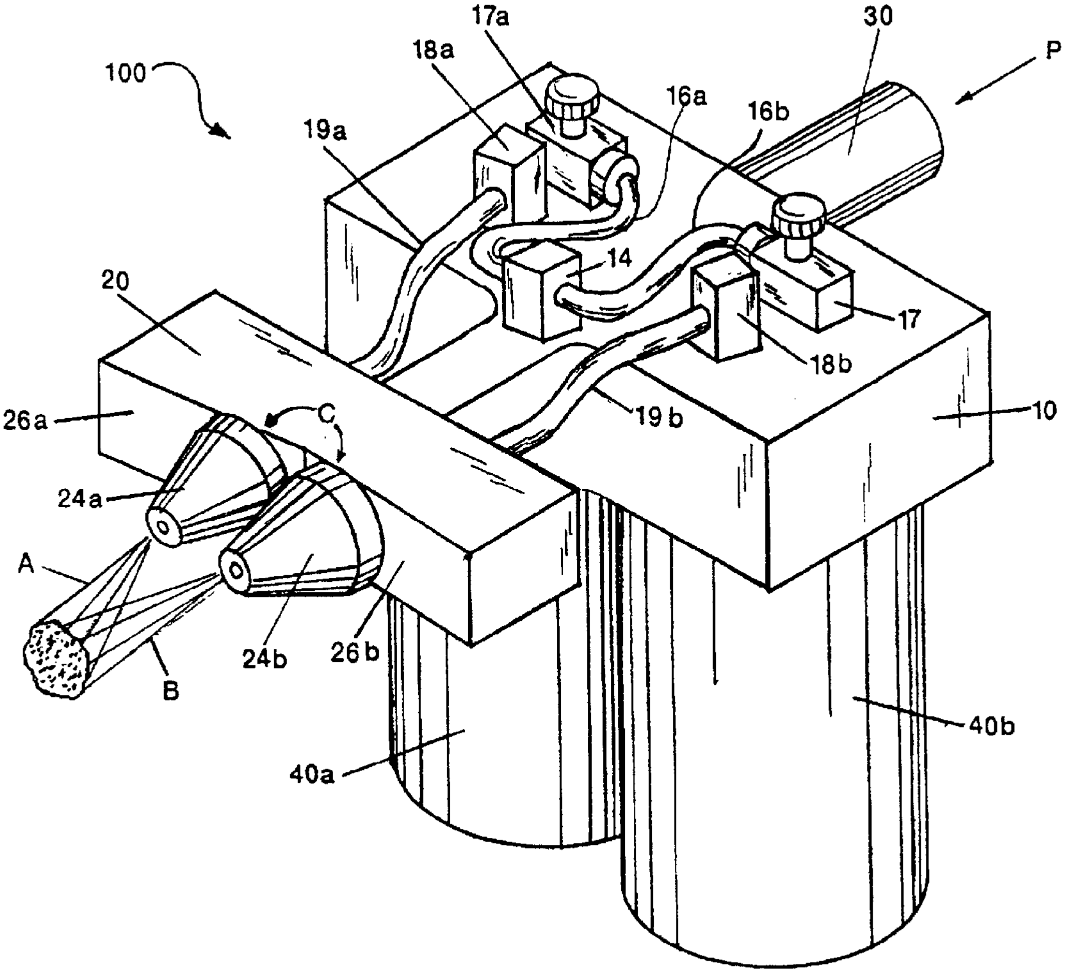
FIG. 1 is an isometric view of a preferred embodiment of the dual spray applicator of the present invention.

Referring to FIG. 1, an applicator 100 according to one embodiment of the present invention is shown. The applicator 100 consists generally of main body 10, having a spray head 20 attached at a distal end and a pressure inlet 30 attached at a proximal end thereof. Reservoirs 40*a* and 40*b* are shown attached to main body 10 at a lower surface thereof. Spray head 20 has faces 26*a* and 26*b* at a distal end thereof that receive atomizers 24*a* and 24*b* respectively. A bifurcated tap 14 and flow rate valves 17*a* and 17*b* on an upper surface of main body 10 are connected by feed lines 16*a* and 16*b*. Connection taps 18*a* and 18*b* are connected to atomizers 24*a* and 24*b* respectively by feed lines 19*a* and 19*b*. These components, described in greater detail below, are preferably made of medical grade material such as metal or plastic, however it is to be understood that other suitable materials may be used.

Figure 2:
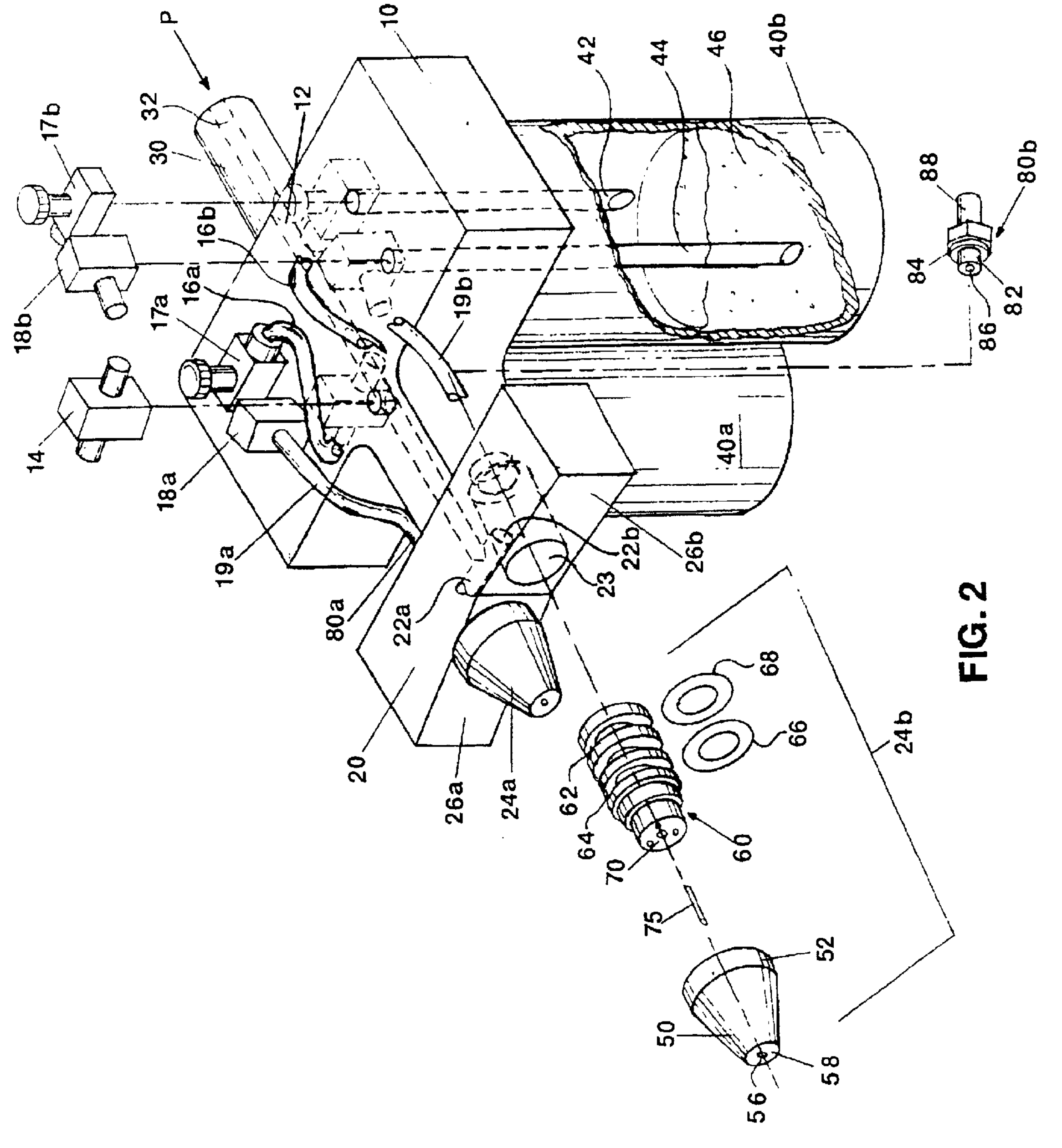
FIG. 2 is a partially exploded view of the embodiment FIG. 1.

As described below, a first series of interconnected conduits defining a first fluid passage extends from pressure inlet 30 through main body 10 to spray head 20. With reference to FIG. 2, pressure inlet 30 is attached to main body 10 as by a threaded or press-fit connection (not shown) and has coaxial bore 32 disposed therein. Main body 10 has a main bore 12 therein that is in fluid communication with coaxial bore 32 and extends through main body 10 to its distal end.

Spray head 20 is connected to main body 10 as by fasteners such as screws or may have interlocking components that may be press fit (not shown). Divergent bores 22*a* and 22*b* are in fluid communication with main bore 12 at a proximal end of spray head 20 and extend therethrough, terminating at atomizers 24*a* and 24*b* respectively thereby establishing a fluid passage between the atomizers and pressure inlet 30.

A second series of interconnected conduits defining a second fluid passage connects pressure inlet 30 to reservoirs 40*a* and 40*b* and therethrough individually to spray head 20, the components associated with reservoir 40*b* shown in an exploded view. Specifically, bifurcated tap 14 located on a top surface of the main body 10 is in fluid communication with main bore 12. Feed lines 16*a* and 16*b*, such as flexible hoses, establish fluid communication between bifurcated tap 14 and valves 17*a* and 17*b* respectively. Valve 17*b* in turn is in fluid communication with the interior of reservoir 40*b* via an inlet conduit 42 such as a hollow needle or luer connection. Likewise, valve 17*a* is in fluid communication with reservoir 40*a* via a similar inlet conduit (not shown). Valves 17*a* and 17*b* may be flow rate valves such as those well known in the art which selectively permit manual adjustment of fluid flow therethrough, or any other means appropriate to regulating fluid flow.

Outlet conduit 44 extends from the interior of reservoir 40*b* where it is in fluid communication with the contents 46 of reservoir 40*b* which are preferably either fibrinogen or thrombin and may include FMB or cells. Outlet conduit 44 terminates at connection tap 18*b*. A similar outlet conduit (not shown) extends from the interior of reservoir 40*a* where it is in fluid communication with the contents thereof and terminates at connection tap 18*a*. The outlet conduits may be of a luer connection type such as that of the inlet conduit 42, or a submersible tube or large-bore needle. Thus, the second fluid link incorporates the interior of reservoirs 40*a* and 40*b*.

Feed lines 19*a* and 19*b* extend the second fluid link from the connection taps 18*a* and 18*b* respectively to atomizers 24*a* and 24*b* respectively of spray head 20. Atomizers 24*a* and 24*b* have a similar construction, FIG. 2 providing an exploded view of the components of atomizer 24*b*. Nozzle 50 is generally frusto-conical having tip 58 and annular base 52. Aperture 56 is a bore which extends through tip 58 through frusto-conical nozzle 50. Carburetor 60 is generally cylindrical and is provided with circular face 70 and annular shoulders 62 and 64 which receive o-rings 66 and 68.

Figure 3A:
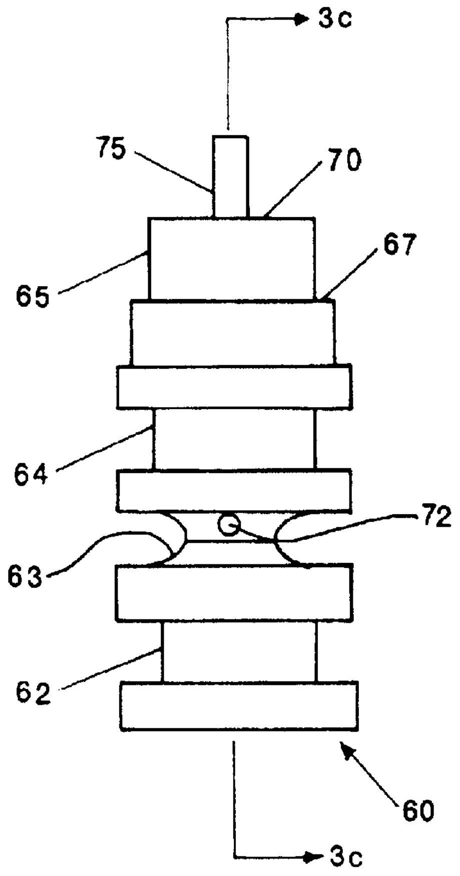
FIG. 3*a* is a plan view of the atomizing carburetor of the present invention.
Figure 3B:
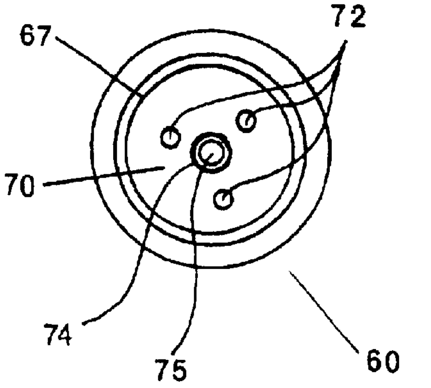
FIG. 3*b* is a cross-section view of the outlet of the carburetor.
Figure 3C:
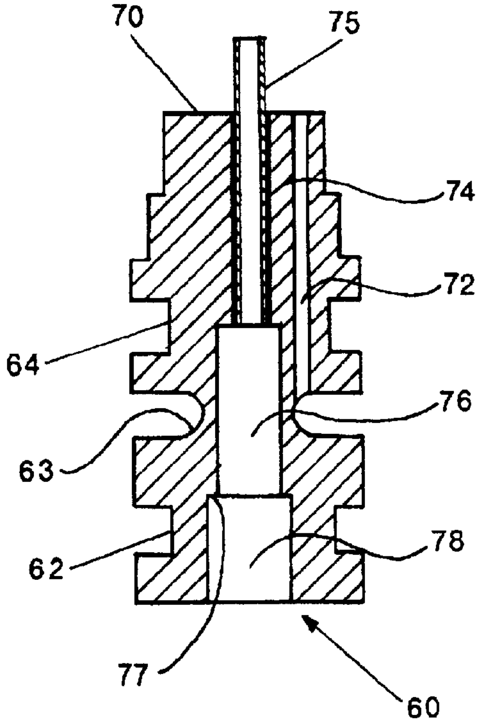
FIG. 3*c* is a longitudinal cross section view of the carburetor.

Carburetor 60 is shown in greater detail in FIGS. 3*a*–3*c*. In FIG. 3*a*, annular shoulders 64 and 62 are shown on either side of annular propellant channel 63 having a plurality of propellant bores 72 therein. Mounting step 65 is preferably a cylindrical ledge shown having a cross-section defining face 70 at one axial end thereof and terminating at a back stop 67 larger in diameter. Needle 75 is shown protruding from face 70. FIG. 3*b* shows face 70 having a plurality of propellant bores 72 and discharge bore 74. FIG. 3*c* is a cross-section view of carburetor 60 illustrating one of propellant bores 72 which extend axially from propellant channel 63 to face 70. Discharge bore 74 extends axially through the carburetor 60 and comprises intermediate bore 76 and inlet bore 78. Needle 75, which ideally has a bore between 16 and 27 gauge, is shown press-fit into and extending along discharge bore 74 terminating at intermediate bore 76. Due to the larger diameter of inlet bore 78 relative to intermediate bore 76, the interface therebetween creates annular ridge 77.

Figure 6:
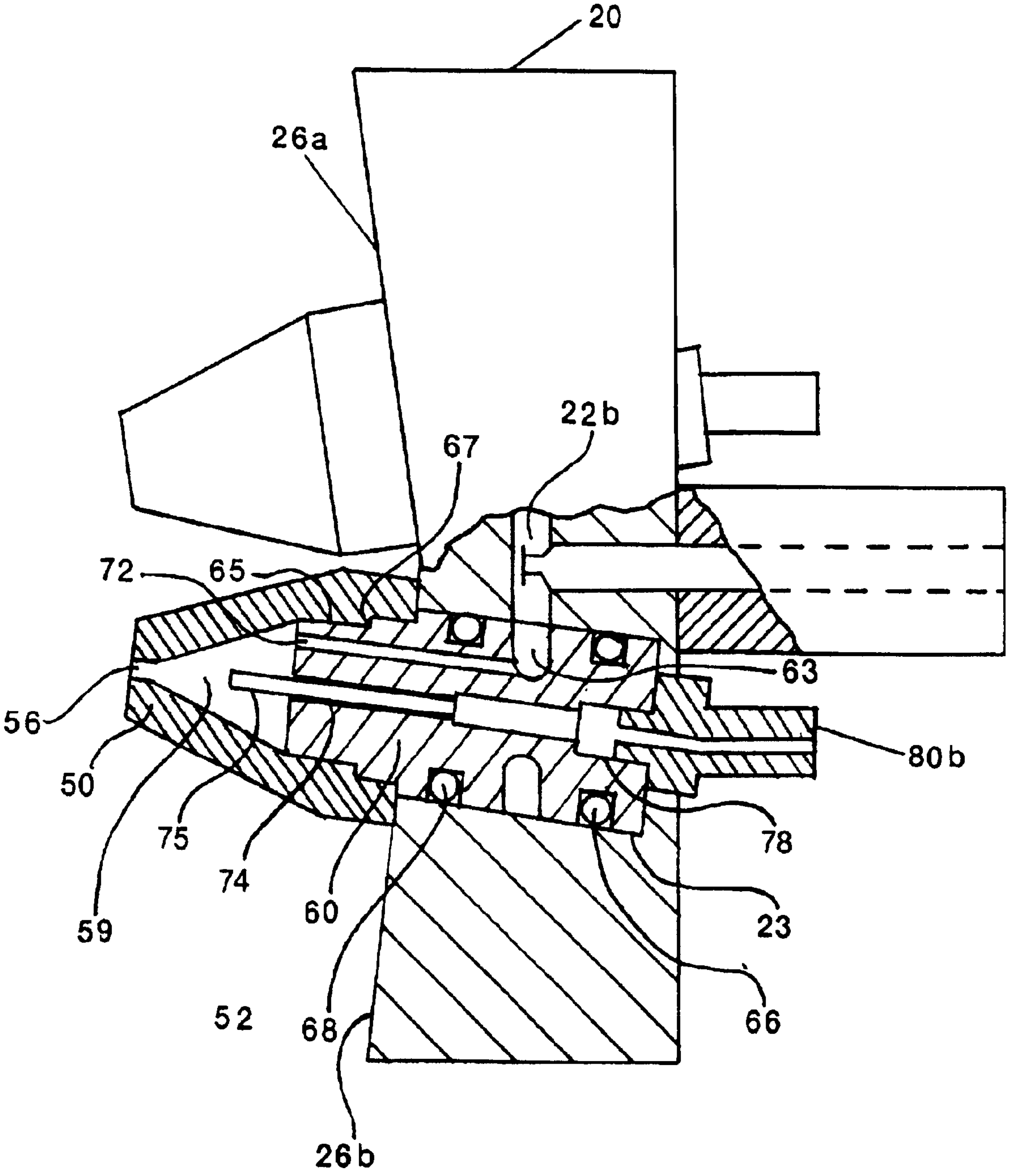
FIG. 6 is a partial cross-section view of the spray head of FIG. 5.

As shown in FIG. 2, spray head 20 has bore 23 having a diameter sufficient to receive carburetor 60. When assembled into spray head 20 as shown in FIG. 6, the carburetor 60 is inserted into bore 23 such that the o-rings 66 and 68, which are preferably formed of resilient material such as viton, butyl rubber or similar medical-grade material, seal against the bore 23. In place within bore 23, rings 66 and 68 cooperate to form a sealed chamber linking propellant channel 63, and propellant bores 72, with bore 22*b*. Needle 75 has an axial bore ideally between 16 and 27 gauge and is press fit into discharge bore 74. Nozzle 50 is attached to carburetor 60 as by a press fitting annular base 52 onto mounting step 65 up to back stop 67. Thus, nozzle 50 forms aerosol chamber 59 when fitted over carburetor 60. Union 80*b* is shown angled to be parallel with the centerline of the sprayer, facilitating removable mounting of head 20 onto the sprayer.

As shown in FIG. 2, union 80*b* has axial bore 86 that communicates with feed line 19*b* which is attached at flange 88. Union 80*b* also has flange 82 which is inserted into inlet bore 78 (FIG. 3*c*) and secured to carburetor 60 as by a press-fitting into inlet bore 78. Seal 84, such as a silicone washer, seals the union 80*b* to the carburetor 60. Union 80*a* is similarly inserted into the carburetor (not shown) of atomizer 24*a*.

Atomizers 24*a* and 24*b* are understood to have similar constructions as described above from union 80*b* to nozzle 50 and are attached to faces 26*a* and 26*b* of spray head 20 respectively as shown in FIGS. 2 and 6. Faces 26*a* and 26*b* are angularly offset relative to each other at an angle shown in FIG. 1 as C such as 194° so that the axes of atomizers 24*a* and 24*b* intersect externally to applicator 11 at an angle, for example of 14°, that defines the focal point of the applicator during use as described in detail below. Thus, a second fluid passage is established between the atomizers 24*a* and 24*b* and pressure inlet 30.

Reservoirs 40*a* and 40*b* are hermetically sealed to the main body 10 by a docking mechanism such (not shown). The docking mechanism may be a threaded or bayonet-type connection sealed with medical grade neoprene or butyl rubber, or any other suitable means for establishing a hermetic seal to prevent the escape or contamination of the contents of the reservoirs 40*a* and 40*b*. The dock mechanisms should also be able to prevent leakage of fluid pressure from the interior of the reservoirs to the ambient atmosphere. One such dock mechanism is described in detail below.

During operation, a source of fluid pressure, shown in FIG. 2 as P, preferably clean compressed gas, is supplied to pressure inlet 30. Preferably, the pressure source is provided with a means for selectively interrupting the flow of gas into pressure inlet 30, such as a trigger valve commonly known in the art to permit the pressure to be controlled by the user's finger or thumb. The source may also be self-contained, such as in the form of a small pressurized gas cannister also well known in the art.

When the compressed gas enters the pressure inlet 30, it flows simultaneously through the two fluid passages defined above. Specifically, after passing through coaxial bore 32, to main bore 12 and through divergent bores 22*a* and 22*b* to the respective carburetors 60 of atomizers 24*a* and 24*b*, the gas is directed into propellant channel 63 by the seal created by w-rings 66 and 68 against bore 23 (FIG. 6). Thus, the compressed gas exits the carburetor via propellant bores 72 into aerosol chamber 59 and into the ambient environment through aperture 56 in nozzle 50 of both atomizers 24*a* and 24*b* simultaneously, according to the first fluid passage defined above.

Ideally, the source of compressed gas is at a sufficiently high pressure, and the divergent bores 22*a* and 22*b* or other bores in the first fluid passage have a sufficiently small diameter that a significant positive back-pressure relative to the ambient environment is maintained in main bore 12. The positive back-pressure drives a fraction of the compressed gas to flow from main bore 12 into bifurcated tap 14 and from there through feed lines 16*a* and 16*b* to valves 17*a* and 17*b* respectively. Valves 17*a* and 17*b* are preferably adjustable flow rate valves that, when open, permit a variable fraction of the pressurized gas to flow into reservoirs 40*a* and 40*b* through inlet conduits such as 42. Because reservoirs 40*a* and 40*b* are hermetically sealed, the flow of compressed gas into the reservoirs pressurizes the individual contents 46 of the reservoirs 40*a* and 40*b* relative to the ambient environment.

Figure 8:
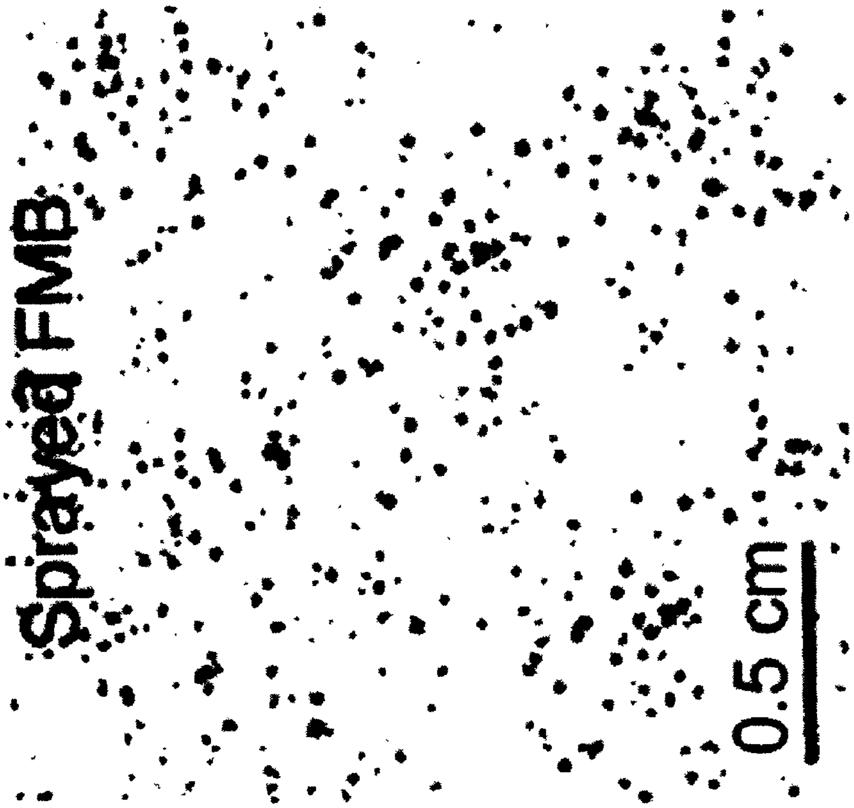
FIG. 8 is an example of methylene-blue stained FMB sprayed in fibrin by an applicator based on FIGS. 1 or 4 onto a flat surface.

The pressure thus applied to the contents of reservoirs 40*a* and 40*b* biases them to flow from the reservoirs through outlet conduits 44 to connection taps 18*a* and 18*b*. The outlet conduits 44 must be oriented to be in fluid communication with the contents 46 of reservoirs 40*a* and 40*b* respectively during use to ensure that compressed gas is not lost through the outlet conduits. Preferably, the outlet conduits 44 are submerged below the hydrostatic level of the contents when the applicator 100 is oriented for use. Feed lines 19*a* and 19*b* carry the contents from connection taps 18*a* and 18*b* respectively to unions 80*a* and 80*b* respectively through which the contents flow into discharge bore 74 of carburetors 60. The respective contents 46 are then forced through the corresponding needles 75 resulting in a mixing of the contents with the streams of compressed gas in the aerosol chamber 59 wherein the contents 46 are atomized, issuing from apertures 56 of atomizers 24*a* and 24*b* thus spraying the respective atomized contents convergently as component streams A and B shown in FIG. 1. An example of methylene blue-stained FMB sprayed in fibrin from a sprayer based on the above embodiment onto a flat surface is provided in FIG. 8.

Thus, the fibrin applicator of the present invention functions to automatically deliver and atomize the components of fibrin upon application of a single supply of compressed gas P. Selective actuation of the compressed gas supply as by a trigger means (not shown) provides a controllable application of fibrin.

Valves 17*a* and 17*b* can be configured to deliver different volumes of components 46 from the applicator 100. For example, by opening valve 17*b*, the volume of compressed gas introduced into the interior of reservoir 40*b* is increased, thereby increasing the pressure on component 46 relative to the ambient environment. Therefore, the wider valve 17*b* is opened, the greater the flow of component 46 to atomizer 24*b*. Conversely, closing a valve tends to restrict the flow of a component from a reservoir. In this manner, the applicator 100 can easily be configured to deliver a precise ratio of components 46 in reservoirs 40*a* and 40*b* relative to each other from the applicator during use. Alternatively, the ratio can be set by the relative diameters of needles 75 in cases where the applicator does not require frequent tuning. Although the rate of fibrin delivery of the applicator 100 is proportional to the magnitude of pressure of compressed gas P, the ratio of components to each other remains constant. This reduces the waste of a component due to application of a sub-optimal ratio of components.

Furthermore, the configuration of the outlet conduits 44 and needles 75 the discharge tips 28*a* and 28*b* can be modified to facilitate the specific characteristics of components 46. For example, in the case of fibrinogen carrying a suspension of FMB or cells, an outlet conduit with a bore compatible with the diameter of the microbead particle would preferably be selected. Likewise, a needle could be selected having a bore that easily accommodates the delivery of microbeads from the applicator without clogging the second fluid passage. Similarly, the portion of the second passage between the reservoirs 40*a*, 40*b* and atomizers 24*a*, 24*b* preferably avoids lengthy or labyrinthine paths that may result in sedimentation of suspended particles.

Additionally, pinch valves (not shown) may be provided in feed lines 19*a* and 19*b* between connection taps 18*a*, 18*b* and atomizer 24*a*, 24*b*, respectively. The pinch valves such as those commonly available selectively interrupt the flow of fluids through the feed line 19*a* and 19*b*, respectively and are actuated by a control means such as a trigger mechanism or an electrically operated solenoid.

During operation, the fibrin applicator 100 using pinch values functions in most respects as disclosed with respect to FIG. 2 above. Specifically, a pressurized fluid "P" such as a clean compressed gas is provided at pressure inlet 30. The compressed gas is then distributed between atomizers 24*a* and 24*b* following the first fluid pathway shown in detail in FIG. 2, and to valves 17*a* and 17*b* respectively via bifurcated tap 14, following the second fluid pathway.

The result upon application of compressed gas "P" is a tendency for the components contained within reservoirs 40*a* and 40*b* to be forced from said reservoir and toward atomizers 24*a* and 24*b* simultaneously with the stream of compressed gas that atomizes the components. In the embodiment of FIG. 1, for example, the addition of pinch valves permits intermittent application of fibrin without interrupting the flow of pressurized gas from the atomizers thus ensuring complete expulsion of the fibrin components delivered to the atomizer. When applying fibrin glue with the applicator of the present embodiment, such pinch valves serve to ensure that none of the relatively precious components that make up the fibrin are wasted.

Figure 4:
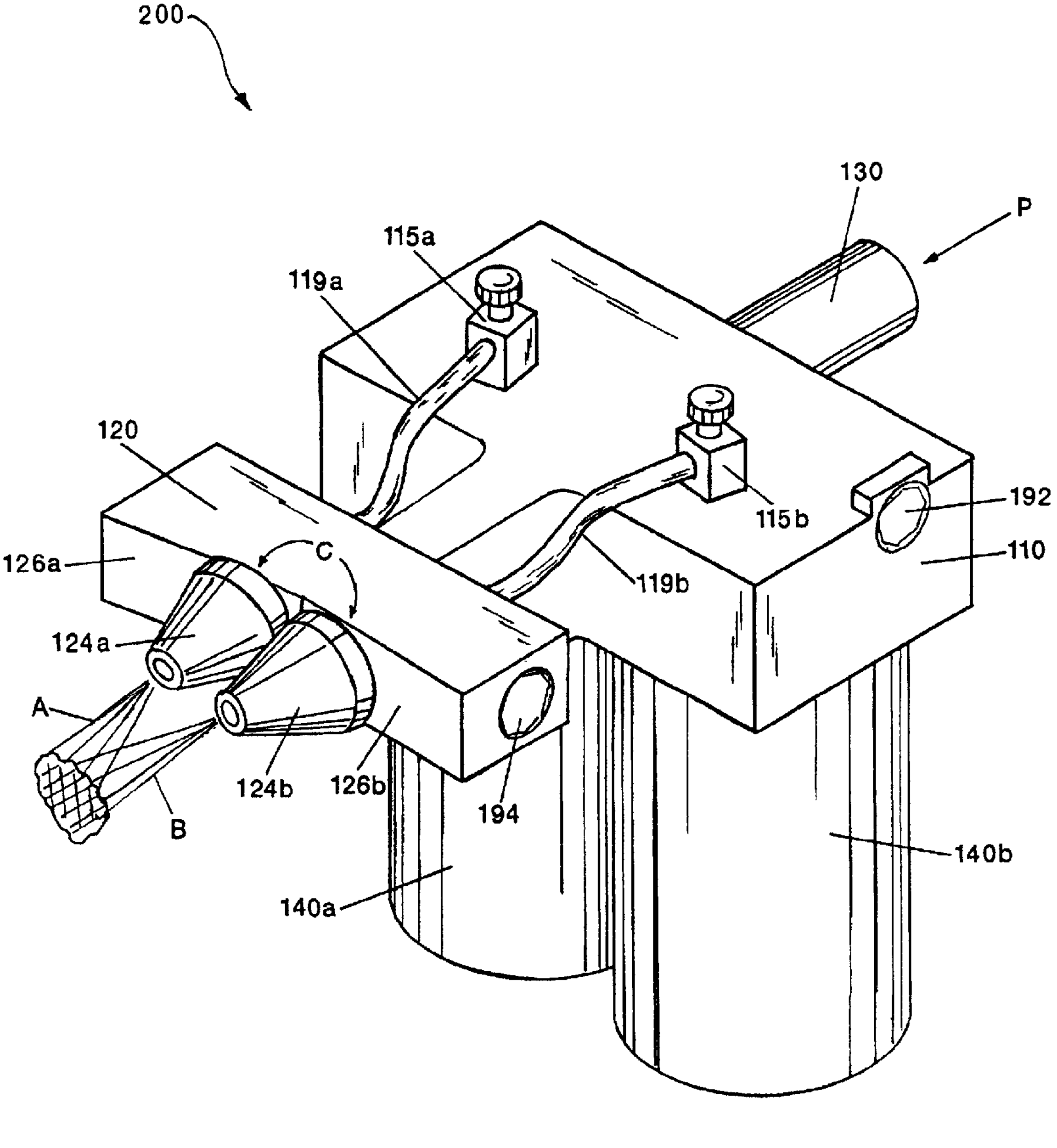
FIG. 4 is an isometric view of another preferred embodiment of the spray applicator of the present invention.

FIG. 4 shows an alternate embodiment 200 of the fibrin applicator of the present invention. The applicator 200 consists generally of a main body 110 having a spray head 120 attached at a distal end and a pressure inlet 130 attached at a proximal end thereof. Reservoirs 140*a* and 140*b* are attached to main body 110 at a lower surface thereof. Spray head 120 has faces 126*a* and 126*b* at a distal end thereof that receives atomizers 124*a* and 124*b* respectively. Flow rate valves 115*a* and 115*b* on an upper surface of main body 110 are connected by feed lines 119*a* and 119*b* to atomizers 124*a* and 124*b* respectively. Pressure regulators 192 and 194 are formed in a side surface in main body 110 and spray head 120 respectively. As in the previous embodiments, these components are preferably made of medical grade material such as metal or plastic, however, other suitable material may be used.

Figure 5:
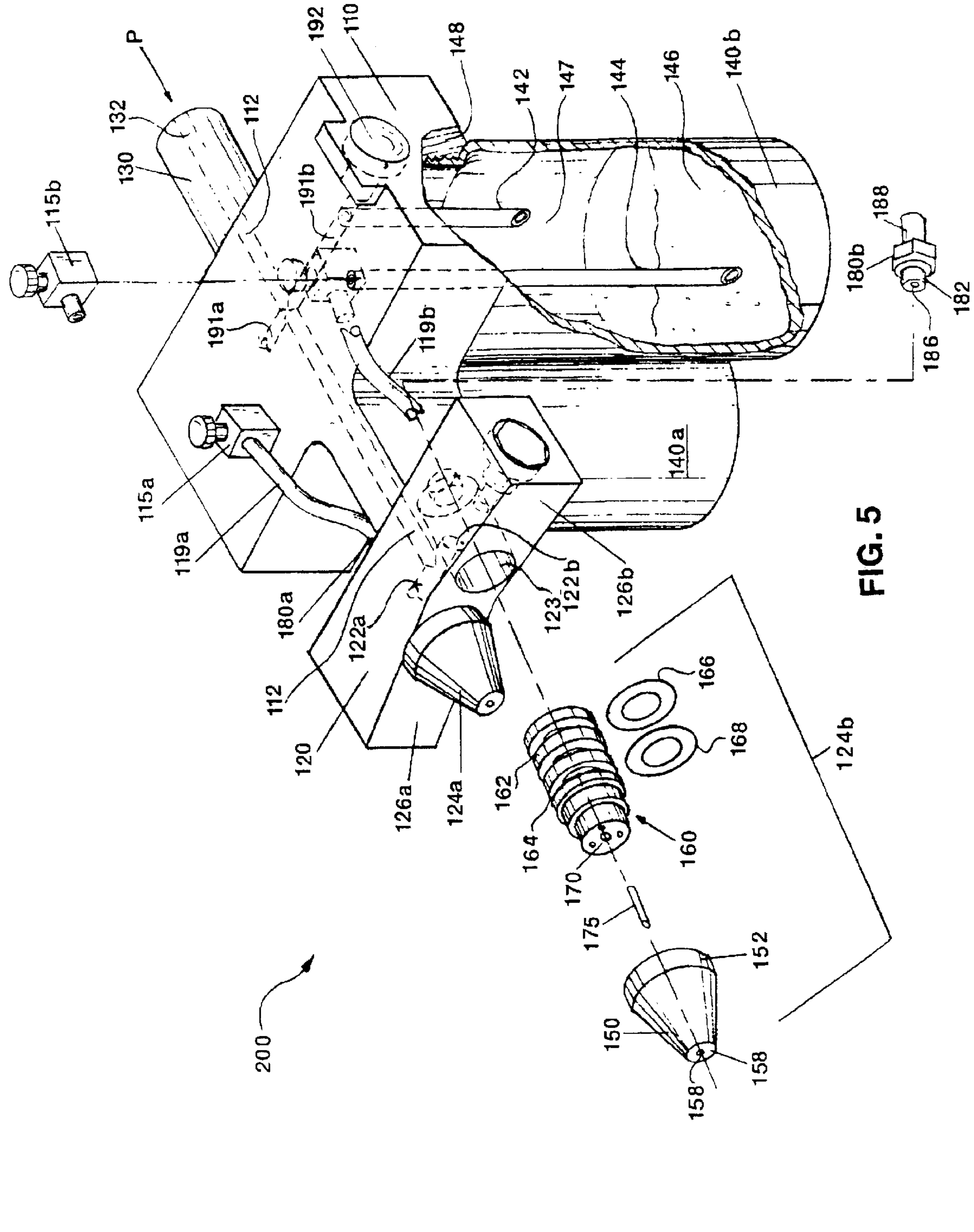
FIG. 5 is a partially exploded view of the embodiment of FIG. 4.

As shown in FIG. 5, a series of interconnected conduits defining a first fluid passage extend from pressure inlet 130 through main body 110 to spray head 120. Pressure inlet 130 is attached to main body 110 as by a threaded or press-fit connection (not shown) and has co-axial bore 132 disposed therein. Main body 110 has a main bore 112 therein that is in fluid communication with co-axial bore 132 and extends through main body 110 to its distal end. Spray head 120 is connected to main body 110 as by fastener or press fit connection (not shown). Divergent bores 122*a* and 122*b* are in fluid communication with main bore 112 within spray head 120 and extends therethrough terminating at atomizers 124*a* and 124*b* respectively, thereby establishing a fluid passage between the atomizers and pressure inlet 130.

A second series of interconnected conduits defining a second fluid passage connects pressure inlet 130 to reservoirs 140*a* and 140*b* and therethrough individually to spray head 120, the components associated with reservoir 140*b* shown in the exploded view in FIG. 5. Specifically, divergent bores 191*a* and 191*b* intercept at main bore 112 establishing fluid communication therewith within main body 110. Bore 191*b* extends from main bore 112 and terminates at pressure regulator 192. Bore 191*b* is also in fluid communication with the interior of reservoir 140*b* via an inlet conduit 142 such as hollow needle or luer connection. Likewise, bore 191*a* extends from main bore 112, terminating at an inlet conduit in fluid communication with the interior of reservoir 140*a* (not shown). Thus, divergent bores 191*a* and 191*b* provide a direct connection between main bore 112 and the respective interiors of reservoirs 140*a* and 140*b*.

Outlet conduit 144 extends from the interior of reservoirs 140*b* where it is in fluid communication with the contents of 146 of reservoir 140*b* which are preferably either fibrinogen or thrombin and may include FMB or cells. The outlet conduit 144 is also preferably a hollow needle or luer connection. Outlet conduit 144 terminates at flow rate valve 115*b*. A similar outlet conduit (not shown) extends from the interior of reservoir 140*a* where it is in fluid communication with the contents thereof and terminates at flow rate valve 115*a*. The outlet conduits may be of a luer connection type similar to that of the inlet conduit 142 or a submersible tube or large bore needle. Flow rate valves 115*a* and 115*b* may be flow rate valves such as those well known in the art for permitting manual adjustment of fluid flow therethrough, or any other means appropriate to regulating fluid flow.

Feed lines 119*a* and 119*b* extend the second fluid link from flow rate valve 115*a* and 115*b* respectively to atomizers 124*a* and 124*b* at spray head 120. Atomizers 124*a* and 124*b* have a similar construction to that of the embodiment shown in FIG. 2, FIG. 5 providing an exploded view of the components of atomizer 124*b*. Specifically, nozzle 150 has tip 158 and base 152. Aperture 156 extends through tip 158 and through nozzle 150. Carburetor 160 is shown having a face 170 and shoulders 162 and 164 which receives o-rings 166 and 168.

As shown in FIG. 5, spray head 120 has bore 123 having a diameter sufficient to receive carburetor 160. When assembled into spray head 120, the carburetor 160 is inserted into bore 123 such that o-rings 166 and 168 seal against bore 123. Thus, a sealed chamber is formed linking carburetor 160 with divergent bore 122*b*. The same structure comprises atomizer 124*a*.

Union 180*b* has bore 186 that communicates with feed line 119*b* which is attached at flange 188. Union 180*b* also has flange 182 which is inserted into and sealed with carburetor 160. Union 180*a* is similarly inserted into the carburetor (not shown) of atomizer 124*a*. Thus, a second fluid passage is established between the atomizer 124*a* and 124*b* and pressure inlet 130.

During operation, a source of fluid pressure, shown in FIG. 5 as P, preferably clean compressed gas having a means for selectively interrupting the flow of said gas is supplied to pressure inlet 130. When the compressed gas enters pressure inlet 130, it flows simultaneously through the two fluid passages defined above. Specifically, after passing through co-axial bore 132 to main bore 112 and through divergent bores 122*a* and 122*b* to the respective carburetors 160 of atomizers 124*a* and 124*b*, the gas is directed into and out of nozzle 150 from carburetor 160 through aperture 156.

Ideally, the source of compressed gas is at a sufficiently high pressure that a significant positive back pressure relative to the ambient environment is maintained in main bore 112. The positive back pressure drives a fraction of the compressed gas to flow from main bore 112 into divergent bores 191*a* and 191*b* thereby pressurizing the interior of reservoir 140*a* and 140*b* respectively.

Thus, the pressure applied to the contents of reservoirs 140*a* and 140*b* biases them to flow through outlet conduit 44 to flow rate valve 115*a* and 115*b*. When the valves are open, the respective contents flow from the reservoirs through feed lines 119*a* and 119*b* to unions 180*a* and 180*b* respectively, through which the contents flow into atomizers 124*a* and 124*b* resulting in a mixing of the contents with the compressed air flowing from carburetor 160 thus atomizing the respective contents convergently as component streams A and B having a focal point defined by angle C of faces 126*a* and 126*b* as shown in FIG. 4.

Thus, the fibrin applicator 200 of the present embodiment functions automatically to deliver and atomize the components of fibrin upon application of a single supply of compressed gas P. In this embodiment however, the result is achieved with fewer parts, as divergent bores 191*a* and 191*b* eliminate the need for a bifurcated tap and the additional connection taps required in the embodiment of FIG. 1. Additionally, fibrin applicator 200 provides pressure regulator 192 at divergent bore 191*b* and pressure regulator 194 at divergent bore 122*b* which can be adjusted to ensure delivery of proper gas pressure to the first and second fluid paths respectively.

Valves 115*a* and 115*b* can be configured to deliver different volumes of individual components 146 from the applicator 200. For example, by opening valve 115*b*, the volume of the liquid expelled from reservoir 140*b* can be regulated relative to the flow of components through valve 115*a*. In this manner, the applicator 200 can be configured to deliver precise ratios of components 146, thus reducing waste due sub-optimal delivery of components. As in he embodiment of FIG. 1, the component ratios can be set by varying the bore of needles 175 in case frequent tuning of the ratios is not required.

The docking mechanism of the present invention is shown in detail in FIG. 5. Specifically, reservoir 140*b* is shown containing component 146 such as a suspension of FMB in fibrinogen, attached to main body 110. Inlet conduit 142 and outlet conduit 144 are shown as hollow bores such as needles wherein outlet conduit 144 is shown submerged below the hydrostatic level of contents 146, and inlet conduit 142 is shown above the hydrostatic level within void 147.

As discussed above, gas entering from divergent bore 191*b* into bore 147 through inlet conduit 142 displaces component 146, forcing it out through outlet conduit 144. The docking connection 148 between reservoir 140*b* and main body 110 must allow for both inlet conduit 142 and outlet 144 to pass into said reservoir 140*b* during insertion thereof onto main body 110. At the same time, it is essential that a fluid-tight seal is maintained between the conduits, main body and reservoir to prevent compressed gas from escaping void 147 and exiting directly into the ambient atmosphere. Such a leak would result in an unpredictable amount of each component discharged during operation of the applicator, altering the ratio of components to each other and wasting component material. Although the structure of applicator 200 of FIGS. 4 and 5 has distinct advantages over applicator 100 of FIGS. 1 and 2 insofar as flow rate valve 115*a* and 115*b* are downstream from any leak of gas from reservoir 140*a* and 140*b*, thereby minimizing the effect of a minor pressure leak, a sufficient leak of gas from either reservoir through its docking connection 148 could result in insufficient pressure within reservoirs 140*a* and 140*b* to propel contents 146 through outlet conduit 144.

Docking connection 148 ideally comprises a union having a threaded connection such as that shown in FIG. 5. In the alternative, a resilient gasket material such as medical-grade rubber or silicon may be disposed between the main body 110 and reservoirs 140*a* and 140*b*. Further, reservoirs 140*a* and 140*b* may comprise a vial having at one end a self-sealing septum capable of removably receiving the inlet conduit 142 and outlet conduit 144 without breaking the seal between the interior of reservoirs 140*a* and 140*b* and the ambient environment. In such a configuration, inlet conduit 142 and outlet conduit 144 ideally share a single needle having two bores (not shown). In such a configuration the docking connection 148 could be disposed for example on the top surface of main body 110 allowing for inverted loading of the reservoirs.

Figure 9:
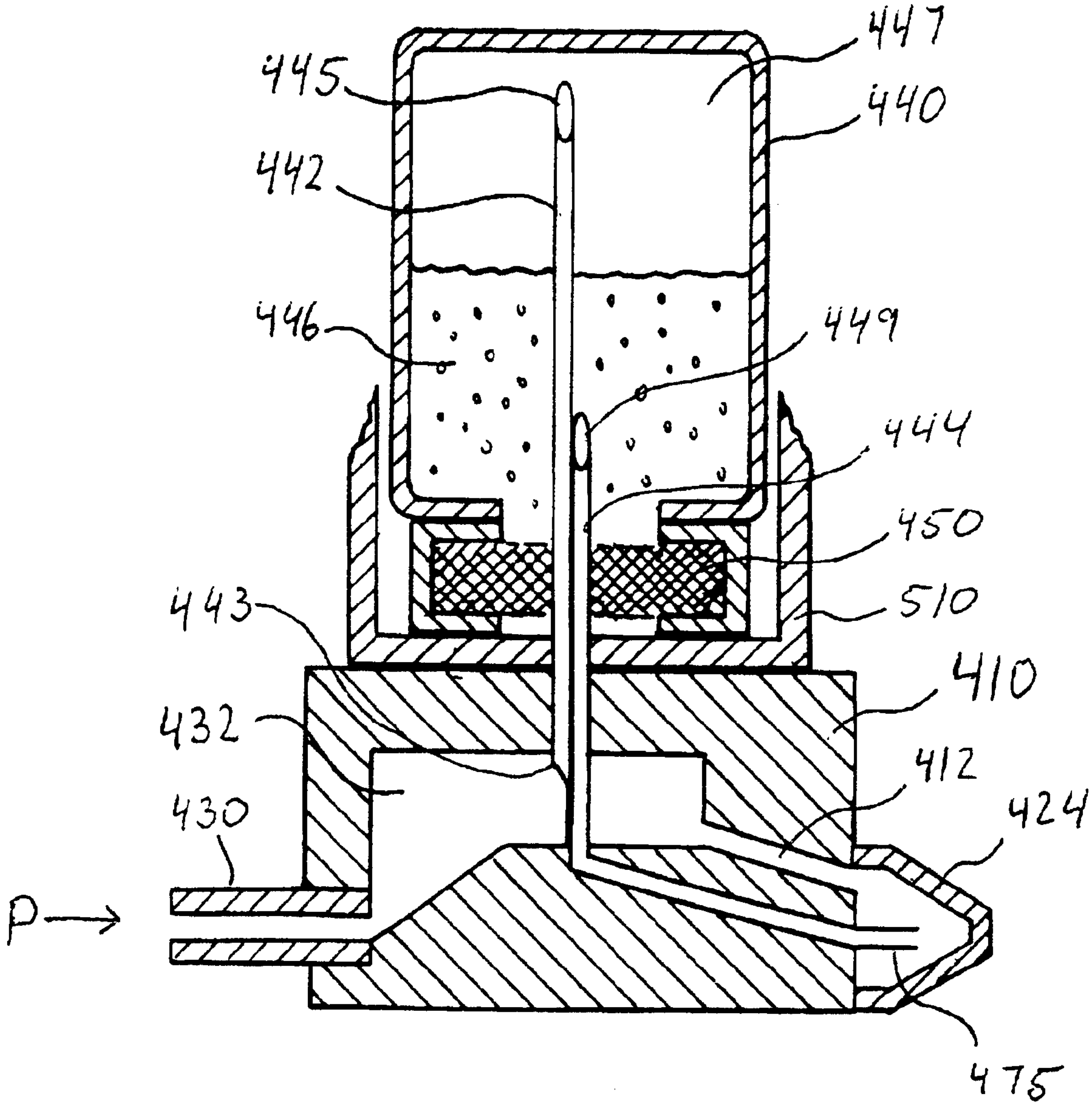
FIG. 9 is a cross-section side view of an alternate embodiment of the present invention incorporating an inverted reservoir mount.
Figure 10:
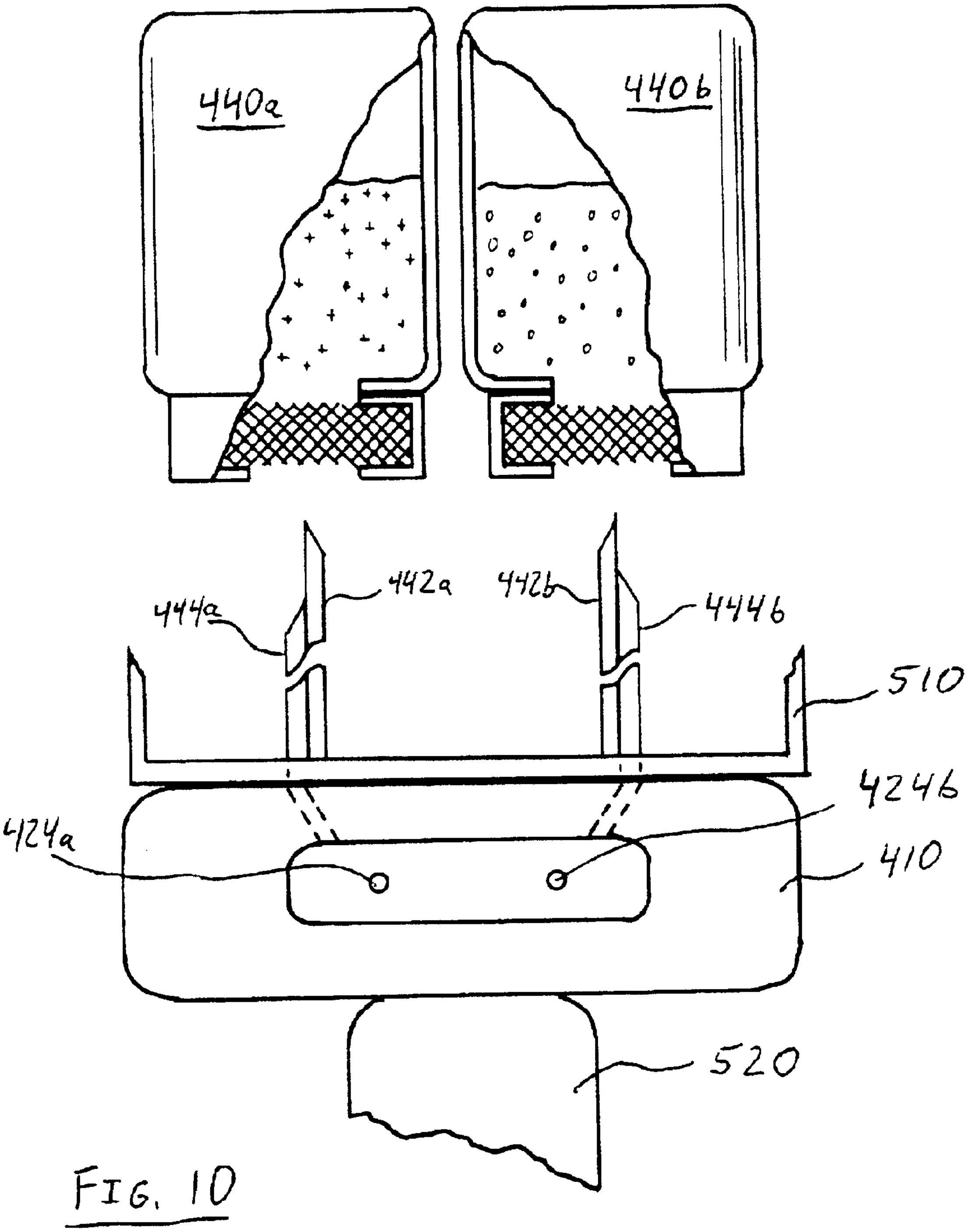
FIG. 10 is a partial cross-section view of the inverted reservoir mount of FIG. 9 showing both reservoirs.

An example of such an inverted loading arrangement is shown in FIGS. 9 and 10. In FIG. 9, a single reservoir 440 of a dual reservoir system is shown as a vial having self-sealing septum 450 which removably receives an inlet conduit 442 and outlet conduit 444 which are shown in a dual needle configuration. In FIG. 9 body 410 is shown having frame 510 attached at an upper surface thereof for guiding reservoir 440 onto inlet/outlet conduits 442/444. Pressure inlet 430 disposed at the rear of body 410 is in fluid communication with air passage 432 and extends to atomizer 424 via bore 412.

Inlet conduit 442 is a hollow needle having openings 443 and 445 at opposite ends thereof. Opening 443 is in fluid communication with air passage 432. Likewise, opening 445 is in fluid communication with the interior 447 of reservoir 440. Outlet conduit 444 is a hollow needle having opening 449 at one end thereof which is in fluid communication with the contents 446 of the reservoir 440. Outlet conduit 444 extends from opening 447 through body 410 and terminates at a discharge orifice 475 within the air chamber defined by atomizer 424.

The dual reservoir arrangement of the present invention is more clearly shown in FIG. 10 where reservoirs 440*a* and 440*b* are shown prior to insertion onto dual inlet/outlet conduit needles 442*a*/444*a* and 442*b*/444*b* respectively. Each of reservoirs 440*a* and 440*b* may have a separate air passage associated with it, which feed gas individually to atomizers 424*a* and 424*b*. Frame 510 is shown attached to an upper surface of body 410 and spray head 420 is shown having atomizers 424*a* and 424*b*. A grip 520 may be attached a to a lower portion of body 410 for use in holding the body by hand.

During operation, a source of fluid pressure, shown in FIG. 9 as P, preferably clean compressed gas having a means for selectively interrupting the flow of said gas, is supplied to pressure inlet 430. When the compressed gas enters fluid passage 432, it flows simultaneously through bore 412 and through inlet conduit 442 via opening 443.

Thus, as shown in FIG. 9, pressure is applied to the contents 446 of reservoir 440 via the introduction of gas into the interior 447 thereof. The contents 446 are thus biased to flow from reservoir 440 via outlet conduit 444 into atomizer 424, where it mixes with compressed gas exiting from bore 412 dispersing contents 446 upon exit from atomizer 424.

The advantages of the docking system disclosed in FIGS. 9 and 10 include the ability to quickly load and exchange vials, the self-sealing design of which is commonly known in the medical arts. Similarly to the previous embodiments, the ratios of components 446*a* to 446*b* may be controlled by varying the diameters of inlet and outlet conduits 442 and 444 for each of reservoirs 440*a* and 440*b*. Additionally, bore 412 may be selectively narrowed to increase back pressure in air chamber 432 resulting in an increase flow of contents 446 from reservoir 440. A separate adjustable valve at bores 412 associated with each of reservoirs 440*a* and 440*b* can also effectively adjust and achieve any desired component ratios.

Figure 7:
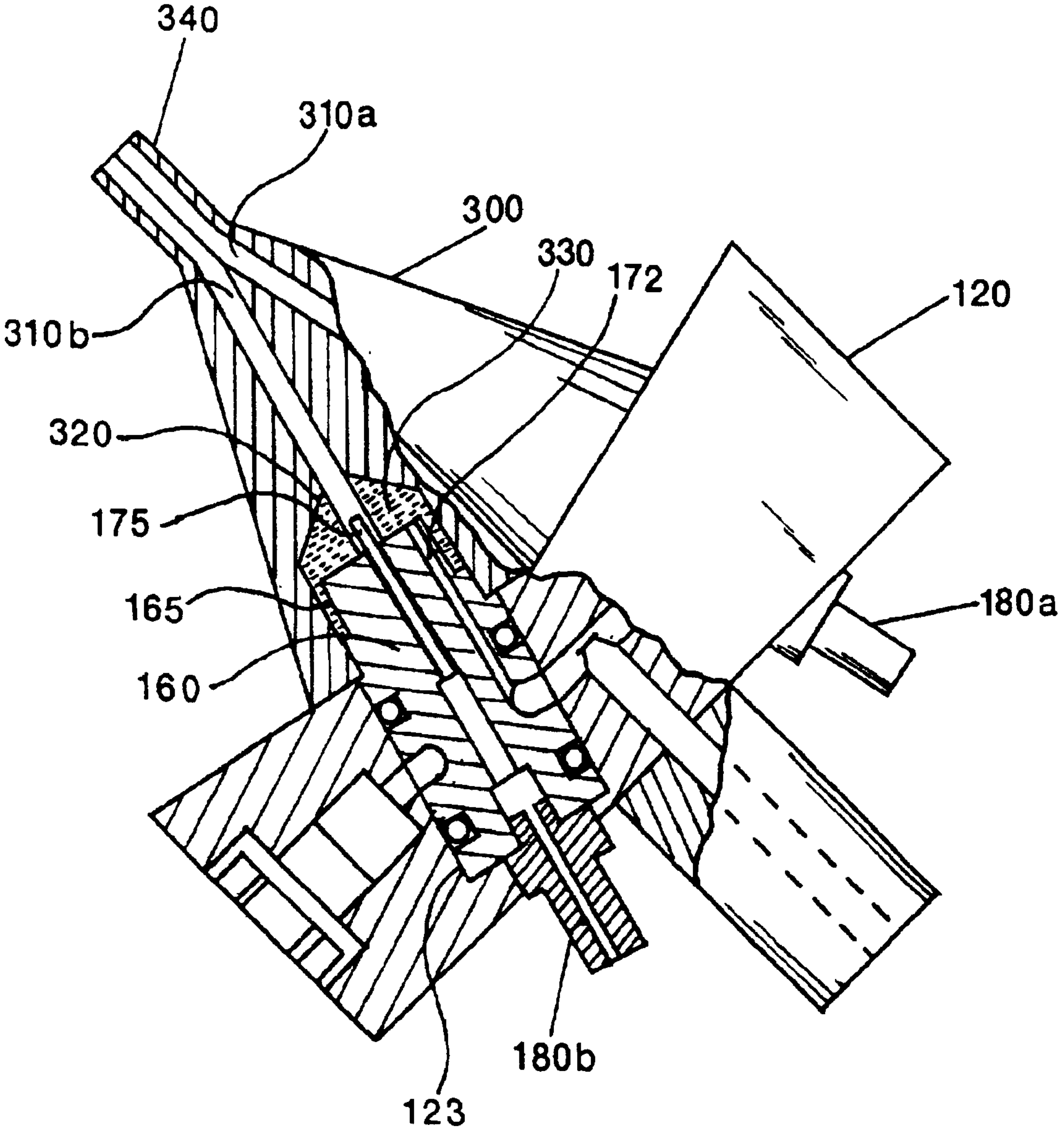
FIG. 7 is a partial cross-section view of an endoscopic delivery head attached to the body of the applicator.

Depending on the configuration of the head, the device 200 of FIGS. 4 and 5 could deliver the fibrin either as a spray as described above or as a topically mixed liquid which coagulates upon mixing of the fibrinogen with the thrombin solution. FIG. 7 shows a detail of a dual-cannula endoscopic appliance mounted on spray head 120 wherein carburetor 160 having needle 175 is shown inserted within bore 123 of spray head 120. To provide for endoscopic application of fibrin, nozzles 150 of atomizers 124*a* and 124*b* (FIG. 5) are shown replaced by endoscopic appliance 300. Therefore, the fibrin applicators, for example, of FIGS. 1 and 4 can easily be converted for endoscopic use by removing the nozzles and installing endoscopic delivery appliance 300 as described below and shown in FIG. 7 with respect to the spray head embodiment of FIGS. 4 and 5.

As shown with respect to carburetor 160, endoscopic appliance 300 has bore 320 which receives mounting flange 165 of carburetor 160, securing the endoscopic appliance 300 to spray head 120. Annular gasket 330 is formed of a compressible, resilient material that seals propellant bores 172. Bore 310*b* is in fluid communication with needle 175. Bore 310*a* is similarly in fluid communication with the needle associated with atomizer 124*a* (FIG. 5), endoscopic appliance 300 engaging said needle and carburetor in a similar manner to that shown with respect to carburetor 160, but blocking the atomizing gas discharge from orifice 172, resulting in a bilateral structure terminating at endoscopic tip 340.

During operation, the fibrin applicator having endoscopic appliance 300 installed functions in a manner similar to that of the embodiment shown in FIGS. 4 and 5 insofar as the contents of each of the two reservoirs are delivered individually to head 120 by the force of a pressurized gas. Thus, the contents are expelled from head 120 (FIG. 7), and are propelled through bores 310*a* and 310*b*. In cases when fibrin glue is to be delivered directly to a tissue defect, an applicator head equipped with endoscopic appliance 300 permits a more precisely directed topical application of fibrin glue via tip portion 340. In this configuration, the fibrin applicator delivers two discrete flows of fibrinogen and thrombin as droplets respectively from bores 310*a* and 310*b*. The fibrinogen and thrombin mix immediately after exiting their respective bores.

When the fibrin applicator is used with endoscopic appliance 300, (FIG. 7) compressed gas flowing through the first fluid passage defined by main bore 112 and the divergent bores 122*a* and 122*b* is prevented from escaping from propellent bore 172 such as that shown in carburetor 160 by annular gasket 330, the carburetor being sealed with respect to divergent bore 122*b* by O-rings 166 and 168. Thus, compressed gas is prevented from entering bores 310*a* and 310*b*.

Although this invention has been described in terms of certain preferred embodiments, other embodiments that are apparent to those of ordinary skill in the art are also intended to be within the scope of this invention. Accordingly, the scope of the present invention is intended to be limited only to the claims appended hereto.

What is claimed is:

1. An applicator for delivering a homogeneous coating of fibrin glue formed from a first component and a second component to a target surface comprising:

a first hermetically sealed reservoir containing said first component and having a first inlet conduit in fluid communication with said first component;

a second hermetically sealed reservoir containing said second component and having a second inlet conduit in fluid communication with said second component;

means for applying positive fluid pressure to said first and second hermetically sealed reservoirs relative to an ambient environment;

a first outlet conduit in fluid communication with said first component and terminated by a first atomizer extending into said ambient environment in a first direction and having a first inner diameter; and a second outlet conduit in fluid communication with said second component and terminated by a second atomizer extending into said ambient environment in a second direction intersecting with said first direction and having a second inner diameter;

wherein application of fluid pressure to said first and second hermetically sealed reservoirs generates a convergent flow of said first and second component at a fixed ratio of said first component to said second component to form said fibrin glue on said surface.

2. The applicator of claim 1 further comprising:

a first valve disposed in said first outlet conduit for selectively controlling said flow of said first component; and a second valve disposed in said second outlet conduit for selectively controlling said flow of said second component.

3. The applicator of claim 2 further comprising a trigger means associated with said first and second valve for simultaneously controlling the flow of said first and second component.

4. The applicator of claim 1 wherein said first inner diameter is different from said second inner diameter.

5. The applicator of claim 4 wherein said first inner diameter compared to said second inner diameter is a predetermined ratio.

6. The applicator of claim 1 wherein said first outlet conduit and said second outlet conduit are separate so that said components intermix external to said applicator.

7. The applicator of claim 1 further comprising: a body having a first dock for removably receiving said first reservoir and a second dock for removably receiving said second reservoir.

8. The applicator of claim 7 wherein said first and second outlet conduit is integral respectively with said first and second dock, wherein said first and second outlet conduit sealingly engages said first and second reservoir respectively.

9. The applicator of claim 8 wherein at least one of said first and second outlet conduit comprises a luer fitting selectively removable from the corresponding of said first and second reservoir.

10. The applicator of claim 1 further comprising at least one pressure regulator associated with said means for applying fluid pressure to permit different rates of pressurization in said first reservoir relative to said second reservoir.

11. The applicator of claim 10 further comprising a first and second control means for independently varying the rates of pressurization in said first reservoir and said second reservoir respectively.

12. The applicator of claim 1 further comprising a tap associated with said means for applying fluid pressure to said first and second atomizer to assist in the respective discharge of said first and second component from said first and second atomizer.

13. The applicator of claim 1 wherein said first component is a thrombin solution and said second component is a fibrinogen solution.

14. The applicator of claim 13 wherein said fixed ratio is sufficient to form the substance fibrin.

15. The applicator of claim 1 wherein at least one of said first and second component carries at least one of a suspension fibrin microbeads or a suspension of cells.

16. The applicator of claim 15 wherein said particles range in size from at least 0.1 to 100 microns.

17. An applicator for delivering a homogeneous coating of fibrin glue formed from a first component and a second component to a target surface, said second component being biologically reactive with said first component comprising;

a first reservoir having a hermetically sealed interior chamber containing said first component;

a second reservoir having a hermetically sealed interior chamber containing said second component;

a body having a first and second dock for receiving respectively said first and second reservoir;

a main bore within said body having an inlet for receiving a pressurized fluid;

a bifurcated tap in fluid communication with said main bore having a first and second inlet conduit in fluid communication respectively with the interior chambers of said first and second reservoirs for delivering said pressurized fluid thereto;

a first outlet conduit in fluid communication with said first component and extending through the interior chamber of said first reservoir and terminating in a first discharge tip having a first orifice for expelling said first component;

a second outlet conduit in fluid communication with said second component and extending through the interior chamber of said second reservoir and terminating in a second discharge tip having a second orifice for expelling said second component;

wherein application of positive fluid pressure relative to an ambient environment to said inlet generates a convergent flow of said first and second component respectively from said first and second discharge tips to form said fibrin glue on said surface.

18. The applicator of claim 17 wherein the said first and second discharge tip comprises a dual-cannula endoscopic catheter.

19. The applicator of claim 17 wherein said first and second discharge tip each comprises an atomizer.

20. The applicator of claim 19 further comprising a second bifurcated tap in said main bore for providing said pressurized fluid to said first and second discharge tips for atomizing said first and second components expelled therefrom.

21. The applicator of claim 17 wherein at least one of said first and second reservoir is selectively removable from said body.

22. The applicator of claim 21 wherein at least one of said first and second outlet comprises, integral with corresponding said first and second dock, a male luer fitting selectively removable from said interior chamber corresponding to said first and second reservoir.

23. The applicator of claim 17 further comprising:

a first valve disposed in said first outlet conduit for selectively controlling said flow of said first component; and a second valve disposed in said second outlet conduit for selectively controlling said flow of said second component.

24. The applicator of claim 23 further comprising a trigger means associated with said first and second valve for simultaneously controlling the flow of said first and second component.

25. The applicator of claim 17 wherein said first outlet conduit has a first inner diameter, and said second outlet conduit has a second inner diameter different from said first inner diameter.

26. The applicator of claim 25 wherein said first inner diameter has a predetermined ratio relative to said second inner diameter.

27. The applicator of claim 17 wherein said first outlet conduit and said second outlet conduit are separate so that said components intermix external to said applicator.

28. The applicator of claim 17 wherein said first and second outlet conduit is integral respectively with said first and second dock, and wherein said first and second outlet conduit sealingly engages said first and second reservoir respectively.

29. The applicator of claim 28 wherein at least one of said first and second outlet conduit comprises a luer fitting selectively removable from the corresponding of said first and second reservoir.

30. The applicator of claim 17 further comprising at least one pressure regulator associated with said bifurcated tap to permit different rates of pressurization in said first reservoir relative to said second reservoir.

31. The applicator of claim 30 further comprising a first and second control means for independently varying the rates of pressurization in said first reservoir and said second reservoir respectively.

32. The applicator of claim 17 wherein said first component is a thrombin solution and said second component is a fibrinogen solution.

33. The applicator of claim 32 wherein said convergent flow of said first and second component takes place at a fixed ratio of said first and second component to each other sufficient to form the substance fibrin.

34. The applicator of claim 17 wherein at least one of said first and second component carries a suspension of particles including at least one of fibrin microbeads or cells.

35. The applicator of claim 34 wherein said particles are fibrin microbeads and range in size from at least 0.1 to 100 microns.

36. The applicator of claim 34 wherein said particles are cells and range in size from at least 0.1 to 100 microns.

37. A method for delivering a homogeneous matrix of fibrin glue and suspended particles on a target surface, said matrix formed from a first component stored in a first hermetically sealed reservoir having a first inlet conduit and outlet conduit and a second component stored in a second hermetically sealed reservoir having a second inlet conduit and outlet conduit at least one of said first and second components carrying a suspension of fibrin microbeads, the method comprising the steps of:

applying a first positive fluid pressure to said first inlet conduit thereby pressurizing said first hermetically sealed reservoir relative to an ambient atmosphere, thereby biasing said first component to flow from said first outlet conduit;

applying a second positive fluid pressure to said second inlet conduit thereby pressurizing second hermetically sealed reservoir relative to said ambient atmosphere, thereby biasing said second component to flow from said second outlet conduit;

regulating the flow of said first component from said first outlet conduit relative to the flow of said second component from said second outlet conduit according to a fixed ratio;

atomizing said flow of said first and second components from said first and second reservoir; and orienting said first outlet conduit relative to said second outlet conduit whereby said atomized flow of said first and second component converge to form a single flow oriented toward said target surface;

whereby said first and second components intermix to form said fibrin glue prior to deposition on said target surface whereby said matrix is formed.

38. The method of claim 37 wherein said first and second positive pressures are of different magnitudes relative to said ambient atmosphere.

39. The method of claim 37 wherein said particles are fibrin microbeads.

40. The method of claim 37 wherein said particles are cells.

41. A method for delivering a homogeneous coating of a biological substance on a target surface, said biological substance formed from a first component stored in a first hermetically sealed reservoir having a first outlet conduit submerged in said first component and extending from said reservoir to an ambient atmosphere, and a second component stored in a second hermetically sealed reservoir having a second outlet conduit submerged in said second component and extending from said reservoir to said ambient atmosphere, the method comprising the steps of:

introducing a first volume of compressed gas into said first hermetically sealed reservoir to create a first positive pressure relative to said ambient atmosphere, thereby biasing said first component to flow from said first outlet conduit at a rate proportional to said first positive pressure;

introducing a second volume of compressed gas into said second hermetically sealed reservoir to create a second positive pressure relative to said ambient atmosphere, thereby biasing said second component to flow from said second outlet conduit at a rate proportional to said second positive pressure;

regulating the pressure applied to said first and second hermetically sealed reservoir according to a fixed ratio;

atomizing said flow of said first and second components from said first and second reservoir; and orienting said first outlet conduit relative to said second outlet conduit whereby said atomized flow of said first and second component converge to form a single flow oriented toward said target surface.

42. The method of claim 41 wherein at least one of said first and second components carries a suspension of fibrin microbeads.

43. The method of claim 41 wherein at least one of said first and second components carries a suspension of cells.

44. The method of claim 42 wherein said biological substance is a matrix of fibrin microbeads set in fibrin glue.

45. A method for delivering a biological substance onto a target surface, said biological substance formed from a first component stored in a first hermetically sealed reservoir having a first out conduit submerged in said first component and extending from said reservoir to an ambient atmosphere, and a second component stored in a second hermetically sealed reservoir having a second outlet conduit submerged in said second component and extending from said reservoir to said ambient atmosphere, the method comprising the steps of:

introducing a first volume of compressed gas into said first hermetically sealed reservoir to create a first positive pressure relative to said ambient atmosphere, thereby biasing said first component to flow from said first outlet conduit at a rate proportional to said first positive pressure;

introducing a second volume of compressed gas into said second hermetically sealed reservoir to create a second positive pressure relative to said ambient atmosphere, thereby biasing said second component to flow from said second outlet conduit at a rate proportional to said second positive pressure;

regulating the pressure applied to said first and second hermetically sealed reservoir according to a fixed ratio;

said flow of said first and second components from said first and second reservoir; and delivering both of said first and second components via a dual-cannula whereby flow of said first and second components mix externally onto said target.

* * * * *

UNITED STATES PATENT AND TRADEMARK OFFICE

CERTIFICATE OF CORRECTION

PATENT NO. : 6,863,660 B2
DATED : March 8, 2005
INVENTOR(S) : Gerard Marx

It is certified that error appears in the above-identified patent and that said Letters Patent is hereby corrected as shown below:

Title page,
Item [73], Assignee, "Hapio Biotech, Inc." should read -- Hapto Biotech, Inc. --

Signed and Sealed this

Nineteenth Day of July, 2005

JON W. DUDAS

*Director of the United States Patent and Trademark Office*